United States Patent [19]

Rathnow et al.

[11] 3,942,388
[45] Mar. 9, 1976

[54] DEVICE FOR THE CONTINUOUS TAKING OF TEST SPECIMENS FROM PULPS OR SLUDGES

[75] Inventors: Erich Rathnow, Bochum; Hans-Joachim Rasch, Herne, both of Germany

[73] Assignee: Klockner-Humboldt-Deutz Aktiengesellschaft, Germany

[22] Filed: Nov. 12, 1973

[21] Appl. No.: 415,131

[30] Foreign Application Priority Data
Nov. 15, 1972 Germany............................ 2255964

[52] U.S. Cl............................................... 73/421 A
[51] Int. Cl.² ......................................... G01N 1/20
[58] Field of Search... 73/421 A, 424, 421 R, 422 R

[56] References Cited
UNITED STATES PATENTS

| | | | |
|---|---|---|---|
| 2,405,951 | 8/1946 | Herrold............................ | 73/421 A |
| 2,670,629 | 3/1954 | Belden............................. | 73/421 A |
| 3,372,596 | 3/1968 | Keller............................... | 73/194 C |

FOREIGN PATENTS OR APPLICATIONS

| | | | |
|---|---|---|---|
| 1,049,127 | 1/1959 | Germany .......................... | 73/421 A |
| 1,075,892 | 7/1967 | United Kingdom............... | 73/421 A |

*Primary Examiner*—Richard C. Queisser
*Assistant Examiner*—Marcus S. Rasco
*Attorney, Agent, or Firm*—Hill, Gross, Simpson, Van Santen, Steadman, Chiara & Simpson

[57] ABSTRACT

A device for taking test samples from a fluid material including passing the material gravitationally downwardly through a first chamber and through a sample divider plate having a plurality of radially extending openings with a sample takeoff passage receiving a sample through one of the openings and directing the sample to a second chamber which is provided with a second sample divider plate also having openings and with a second sample takeoff receiving a sample from one of the openings and directing it to a third chamber having a sample divider with a plurality of openings and taking a sample through one of said openings with a third sample takeoff passage.

10 Claims, 3 Drawing Figures

DEVICE FOR THE CONTINUOUS TAKING OF TEST SPECIMENS FROM PULPS OR SLUDGES

BACKGROUND OF THE INVENTION

The invention relates to a mechanism for continuously taking test specimens or samples, such as from sludges or pulps, wherein the sample is accurately representative of the flow of material. More particularly, the invention relates to a mechanism for flowing fluid material gravitationally downwardly and taking a sample truly representative of the flow and passing that sample to another chamber where another sample is taken representative of flow and thereafter passing the second sample to a third chamber where another sampling is taken.

Sampling devices for test specimens from pulps or sludges have been known before in the art, and an example of such device is shown in German Pat. No. 745,782. In this patent a sampling spoon is moved back and forth and driven by an electric motor which drives the device to move the spoon in arbitrarily regulable periods of time through the stream from which the sample is to be taken. The sampling spoon is carried by an arm driven by the motor and a time switch controls the mechanism so that the samples are taken from the stream of liquid noncontinuously. The sampling spoon is connected with the discharge conduit inclined downwardly through which the test specimen flows to a collector.

The operation of such a sampler requires the constant supply of driving energy and, of course, requires operating parts which exhibit wear with the passage of time. Also, a timing mechanism must be provided which must be reliable and requires that a source of operating power for the timer be provided. Also, by the nature of such a structure, it must operate intermittently, and therefore, it is not possible to actually take a continuous sample, which can lead to inaccuracies in sampling.

An object of the present invention is to provide a mechanism which furnishes a fully representative sample of fluid material, such as liquid sludges or pulps, which avoids disadvantages of samplers heretofore available and by which a truly continuous withdrawal even of an extremely small quantity of a sample is made possible from a large quantity of flow. The mechanism is practical for use in laboratories which have high requirements with respect to the representative nature of the samples and provide such a sample which can be used for analytical control or for supervision of a process.

A feature of the invention is to provide a chamber through which the material flows gravitationally with the lower area of the chamber constructed as a sample divider having a plurality of passage openings. The chamber is constructed so that flow will be fully uniform and representative through each of the passage openings, and the sample is removed through an takeoff passage receiving flow from only one or a small number of the passage openings. Since the passage openings are uniform in size, location, and shape, and relationship to the main flow through the chamber, a fully representative sample is taken, and the flow continues through the chamber with the fluid continuing to mix homogeneously. By the use of gravitational flow, the power requirements of previous devices is eliminated and losses of material occurring due to erratic operation or power failure are eliminated.

In accordance with the principles of the invention, the lower chamber area is constructed rotatably with respect to the upper chamber area, and the lower chamber area has a sample divider plate with the openings being a plurality of radially extending slots which increase in width radially outwardly. By interchange of plates with different size openings or by selectively blocking a portion of the openings in a uniform manner so that the flow through the remaining areas is representative, the quantity of continuous sampling can be controlled.

In providing a divider plate wherein the passage openings are radially extending slots, a uniform impingement of the flow of material against the plate is obtained and is particularly useful in sludges or pulps. In these types of flows, the formation of strands or build-ups of coagulated or concentrations of materials can occur in ordinary devices, but is avoided so that by the taking of samples, the homogeneity of the flow is not destroyed.

In the preferred embodiment, the initial chamber, and subsequent chambers are cylindrically shaped with the inlet discharging tangentially into the upper area of the chambers. This invokes a whirling movement of the liquids to prevent settling out or coagulation which can occur in sludges or pulps, particularly at the area of the inlet where whorls or whirlpools can form having an adverse effect on the even distribution of the material in suspension in the liquid. By continuing the uniform distribution of material throughout the liquid thé quantities of samples drawn off are fully representative and are an average of the flow of the entire quantity of material. This is particularly important wherein statistics to be produced from the samples indicate analytically the results of a process through which the material has been subjected or control the process to which the material is to be subjected later.

In the cylindrical chamber beneath the inlet is arranged a frustoconical distributor shield with a central opening discharging downwardly toward the sample divider plate. This complements the whirling action of the material entering the chamber tangentially. Directly below the frusto-conically shaped downwardly depending skirt is an upwardly extending cone positioned in the center of the distributor plate with the radial openings extending outwardly and arranged symmetrically around the cone. With this arrangement, the flow through the skirt and onto the cone will be distributed uniformly out over the sample divider plate and over the passage openings so that each passage opening is equally impinged as to quantity of material. The sampling is taken from at least one of the passage openings which discharges downwardly into takeoff passage with the takeoff passage feeding to a second chamber constructed similarly to the first chamber, and an takeoff passage from the second chamber delivering to a third chamber from which a sample is taken. Thus, the first sampling removes only a small representative part of the total flow, and the second sampling represents a small representative part of the first sampling, and the third sampling removes only a small representative part of the second sampling so that the final sample is a very minute part of the whole, but truly representative thereof.

In the construction of the chambers, the lower portion is removable so that the sample divider plate can be readily and quickly exchanged to provide a new plate with different size openings for different sample requirements. In the arrangement above described, the several chambers are arranged in sequence so that the fluid continues to flow gravitationally, and the gravitational flow is channeled and handled in such a manner so as to maintain uniform flow about the central axis of each of the chambers and with the flow continued to be agitated in a manner so that the fluid is homogeneous at all circumferential locations. The rejected portion of the first sample and of the second sample are fed back into a main discharge from the main chamber with the entire unit constructed so as to require relatively small headroom and minimum restriction to flow of the fluid being sampled.

Other objects, advantages and features of the invention will become more clear, with equivalent structures and methods which are intended to be covered hereby, in the disclosure of the specification, claims, and drawings in which:

DRAWINGS

DESCRIPTION

Figure 1:
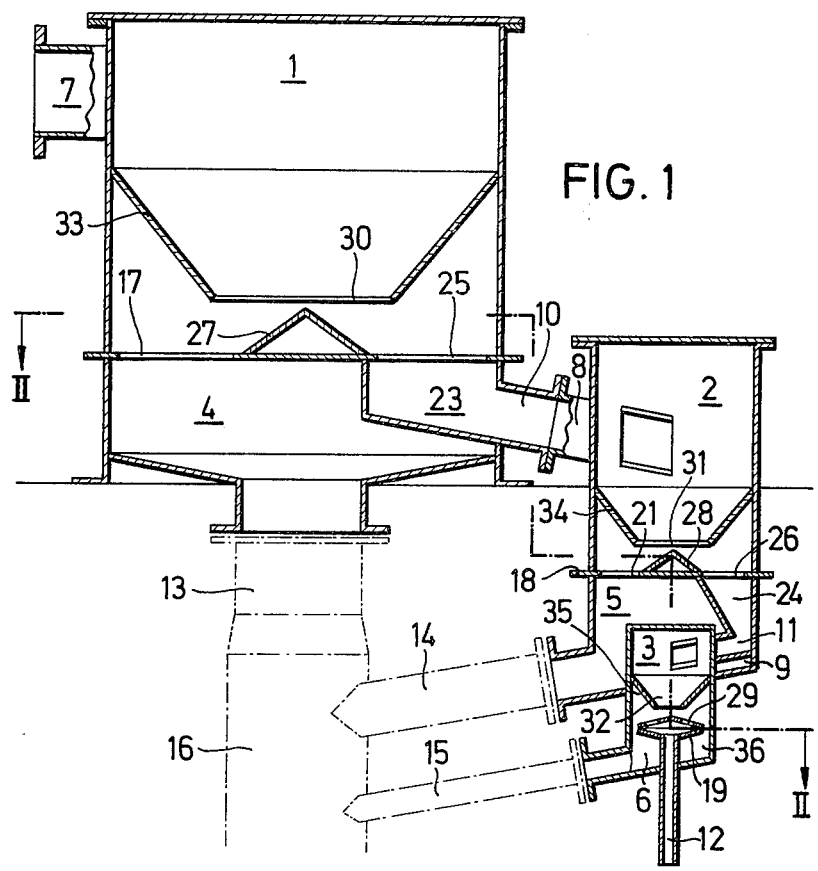
FIG. 1 is a vertical elevational view in section, shown somewhat schematically of a sample taking device constructed and operating in accordance with the principles of the present invention.
Figure 2:
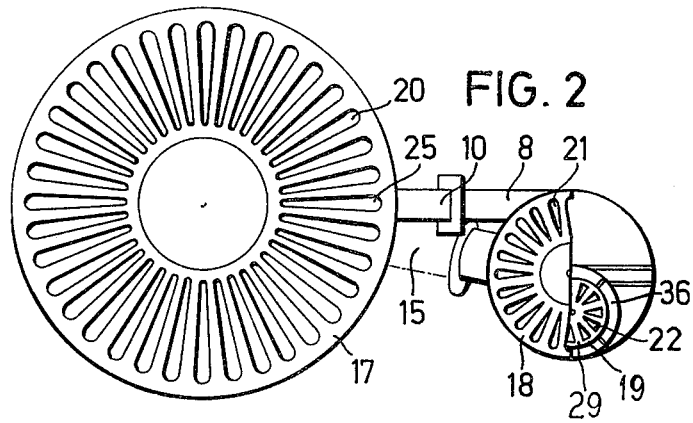
FIG. 2 is a horizontal sectional view taken substantially along line II—II of FIG. 1.

The sample taking device illustrated in FIGS. 1 and 2 preferably includes three chambers 1, 2 and 3 which are interconnected. The chambers and the associated structure are arranged so that a truly representative sample is taken from the complete flow which gravitationally flows through the first chamber, and a sample of that sample removed in chamber 1 is taken in the second chamber, and another sample of the second sample is taken in chamber 3. Thus, the final sample becomes very small, but truly representative of the total flow.

The chambers 1, 2 and 3 are constructed so that each has a discharge housing shown respectively at 4, 5 and 6. Each of the chambers is provided with a tangential inlet shown respectively for the three chambers at 7, 8 and 9. Each of the discharge housings 4, 5 and 6 is provided with a central discharge with the main discharge shown at 13 for chamber 1. The discharges 14 and 15 for chambers 2 and 3 feed back into the main discharge pipe 16 for the first chamber so that the unused or excess amounts of sample material are returned to the main flow. The chamber 3 is uniquely positioned so as to be centrally located, and in essence, pushed partially into the discharge housing 5 of the chamber 2 thereby reducing the amount of vertical and lateral space required.

While three chambers are preferably shown, it will be understood that in some instances, the principles of the invention may be used with a single chamber or with two chambers, or in some instances, more chambers than three may be provided. In accordance with the method, the sample of the fluid material is permitted to flow gravitationally downwardly, and a first representative portion is detoured as a sample, and a portion of that sample is taken as a representative sample and thereafter a portion of that sample portion is taken.

The chambers are preferably cylindrical in shape, and the tangential inlet causes the material to maintain a motion to keep any solids in suspension and uniformly distributed throughout the liquid or to keep any fluid material homogeneous throughout. Extending across the first and second chambers 1 and 2 are sample divider plates 17 and 18. These plates have a plurality of circumferentially uniformly distributed radially extending passage openings 20 and 21 for the plates. These passage openings are arranged symmetrically with respect to the center of each of the plates so that each slot receives a representative flow. One or more of the slots shown at 25 and 26 are in communication with a take-off conduit shown at 10 and 11. These take-off conduits have upper ends 23 and 24 which are open and are in alignment with the slots 25 and 26 so that flow through the slots passes into the conduit. The conduits 10 and 11 discharge tangentially into the chambers 2 and 3 respectively.

At the center of each of the sample divider plates is positioned a cone at 27 and 28 which slopes downwardly and outwardly so that the material flows outwardly and evenly across the radial openings 20 and 21.

Positioned above each of the cones 27 and 28 in the chambers is a downwardly extending frusto-conical distributor shield 33 and 34. The shield has a central opening shown at 30 and 31 for the chambers 1 and 2, and material flows through the opening to the divider plates therebelow.

The chamber 3 may be constructed similarly to 1 and 2 with a plate extending thereacross, but is illustrated as having slightly different construction with a cone shaped divider plate 29 having passage openings 22, positioned in the lower portion of the third chamber. The openings 22 receive a portion of the flow passing down through the third chamber, and the cone has a bottom 19 which channels the sample of material down through the conduit 12 which delivers the final sample. In certain environments it may be desirable not to utilize all of the openings 22, but to provide selective blockages for these openings to reduce the size of the eventual sample which is taken. Because the material is uniformly distributed over the cone 29 by virtue of a downwardly depending frusto-conical skirt 35 in the third chamber, having an opening 32, a uniform flow will occur over all of the openings 22 around the circumference of the deflector 29, which is located in the lower portion 36 of the third chamber.

Figure 3:
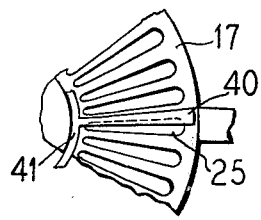
FIG. 3 is a fragmentary view of a portion of FIG. 2 showing additional mechanism for controlling flow volume.

The divider plates 17, 18 and 29 have the elongated slots which increase in width in a radial outward direction. This increase in width provides for representative flow at all radial points of the slot through which the sample is being taken. This permits blocking of a portion of the slot to reduce the portion of the sample being taken. One form of blocking the slot is shown in FIG. 3 wherein a radial vane 40 may be moved circumferentially to block a part of the slot 25. The radial vane may be connected to an inner ring 41 encircling the base of the cone 27 for holding the ring 40 in its stable position, or other structure may be employed for the vane 40. Another way of controlling the amount of sample being taken is to change the plates 17, 18 or 29 with other plates of different sizes. For this purpose, the lower parts of each of the chambers 1 and 2 are removable, or in other words interchangeable, and the unit 19 in the third chamber is interchangeable. It will also be seen that the vane 40 may take various shapes such as having teeth or projections which extend across the slot 25 or may be arranged to progressively cover an inner portion or outer portion of the slot as it is shifted either radially or circumferentially. A similar valving device such as the vane 40 may be provided for the plates 18 29 of the other chambers.

The lower portion of each of the chambers is shown flanged at its upper end, and as will be recognized by those versed in the art, gaskets may be provided to prevent leakage and permit interchangeability.

In operation, the entire flow of material to be tested flows gravitationally downwardly and where material such as liquid or sludge or pulp is to be tested, it is introduced tangentially into the inlet 7, flows in a strongly whirling motion downwardly over the shield 33 through the opening 30 onto the cone 27 and uniformly through each of the slots 20, with the sample portion flowing through the slot 25 into the conduit 10. The sample portion then passes through the conduit 8 tangentially into the second chamber 2, downwardly over the shield 34 onto the cone 28 and uniformly through the slots 21. The usable sample portion is taken through the opening 26 into the conduit 11 and flows tangentially into the chamber 3 whereupon it flows over the skirt 35 through the openings 22 and down to the conduit 12 which provides the final sample. The unused sample portions from chamber 1 flow downwardly through the conduit 13, and the unused portions of the chambers 2 and 3 flow through the conduits 14 and 15 to join the main flow in the pipe 16. In each of the chambers, the liquids continue to whirl maintaining homogeneous flow and the flow remains the same at all circumferential locations of the chamber as well as all radial locations when it reaches the divider plate. With the arrangement described, and in accordance with the principles of the method of the invention, the sample taken is the average of the total quantity. Flow is accomplished and sampling is taken without the use of any power driven or moving parts and gravitational flow is utilized with a mechanism requiring a minimum of space. In addition to being able to sample liquid materials, finely grained pulverulent materials may also be sampled, and divider plates may be chosen of a precise portion of total quantity of flow, and the sample removed can be tested to be representative of flow or it may fed into automatic testing equipment and be used to operate a programmed operating computer to control an overall process in a plant automatically.

We claim as our invention:

1. A mechanism for continuously obtaining a representative sample from a fluid material such as from sludges or pulps comprising in combination:
    a circular chamber with an inlet opening and a main discharge opening;
    a sample divider in the chamber having a plurality of sample openings uniformly distributed circumferentially;
    said inlet opening discharging tangentially into the upper end of said chamber and creating a whirling circular motion in the material in the chamber so that the material has rotary turbulence in passing said sample openings; and
    a sample takeoff passage connected to at least one of said sample divider openings for a sample flow with the remaining flow through the chamber passing through the unconnected sample divider openings to said main discharge opening.

2. A mechanism for continuously obtaining a representative sample from a fluid material such as from sludges or pulps in accordance with claim 1:
    wherein said sample divider is rotational relative to said sample off-take so that with relative rotation selective different numbers of sample divider openings can be placed in communication with said sample takeoff.

3. A mechanism for continuously obtaining a representative sample from a fluid material such as from sludges or pulps in accordance with claim 1:
    wherein said sample divider includes a plate extending completely across said chamber and an annular distributor positioned above said plate.

4. A mechanism for continuously obtaining a representative sample from a fluid material such as from sludges or pulps in accordance with claim 1:
    wherein said sample divider openings comprise a plurality of radially extending slots.

5. A mechanism for continuously obtaining a representative sample from a fluid material such as from sludges or pulps in accordance with claim 1:
    and including a frusto-conically shaped distributor having a central opening and positioned above the sample divider.

6. A mechanism for continuously obtaining a representative sample from a fluid material such as from sludges or pulps in accordance with claim 5:
    and including a conically shaped deflecting body having its apex centrally located relative to the distributor and positioned above said sample divider.

7. A mechanism for continuously obtaining a representative sample from a fluid material such as from sludges or pulps in accordacne with claim 6.
    wherein the sample divider is in the form of a horizontally extending plate and the divider openings are in the form of radially extending slots arranged substantially symmetrically about the center of the chamber.

8. A mechanism for continuously obtaining a representative sample from a fluid material constructed in accordance with claim 1:
    including means for controllably blocking said sample take-off opening.

9. A mechanism for continuously obtaining a representative sample from a fluid material such as from sludges or pulps comprising in combination:
    a circular chamber with an inlet opening and a main discharge opening;
    a sample divider in the chamber having a plurality of sample openings uniformly distributed circumferentially;
    means creating a whirling circular motion in the material in the chamber so that the material has rotary turbulence in passing said sample openings;
    a sample takeoff passage connected to at least one of said sample divider openings for a sample flow with the remaining flow through the chamber passing through the unconnected sample divider openings to said main discharge opening;
    a second chamber receiving sample material from said takeoff passage;
    a sample divider in said second chamber having a plurality of sample openings; and a sample takeoff passage connected with at least one of said divider openings.

10. A mechanism for continuously obtaining a representative sample from a fluid material such as from sludges or pulps in accordance with claim 9. including a third chamber connected to receive material from said takeoff passage from the second chamber;

a sample divider in said third chamber having a plurality of sample openings;

and a sample takeoff passage connected to at least one of said divider openings in the third chamber.

* * * * *